United States Patent [19]

Neduv et al.

[11] 4,139,557

[45] Feb. 13, 1979

[54] METHOD OF PREPARING DIMETHYLACETAMIDE IN PRESENCE OF MoO₃ CATALYST

[76] Inventors: Mikhail B. Neduv, ulitsa K. Marxa, 24, kv. 8; Vladimir I. Bazakin, ulitsa Kommunisticheskaya, 1, kv. 32; Taisia I. Komarenko, ulitsa Deputatskaya, 8, kv. 45; Svetlana M. Zenchenko, ulitsa, K. Marxa, 14, kv. 5, all of Shostka Sumskoi oblasti; Zinaida F. Kirpichnikova, pereulok Tsulukidze, 14, kv. 26, Tbilisi; Igor G. Gakh, ulitsa Shevchenko, 23, kv. 58, Shostka Sumskoi oblasti, all of U.S.S.R.

[21] Appl. No.: 754,435

[22] Filed: Dec. 27, 1976

[51] Int. Cl.² .............................................. C07C 102/00
[52] U.S. Cl. .................................................. 260/561 R
[58] Field of Search ..................................... 260/561 R

[56] References Cited

U.S. PATENT DOCUMENTS

| 1,582,675 | 4/1926 | Fick .................................. | 260/561 R |
| 3,468,919 | 9/1969 | Kilsheimer et al. ............. | 260/561 R |
| 3,580,968 | 5/1971 | Kuraishi et al. ................. | 260/561 R |
| 3,763,234 | 10/1973 | Brill .................................. | 260/561 R |
| 3,801,610 | 4/1974 | Werdehausen ................... | 260/561 R |
| 3,816,483 | 6/1974 | Werdehaussen et al. ........ | 260/561 R |

FOREIGN PATENT DOCUMENTS 48-16894  5/1973  Japan.

OTHER PUBLICATIONS

Merck Index, 7th edition, 1960, p. 688.

*Primary Examiner*—Allen B. Curtis
*Attorney, Agent, or Firm*—Lackenbach, Lilling & Siegel

[57] ABSTRACT

A method of preparing dimethylacetamide which comprises interaction of acetic acid and dimethylamine. The thus-prepared dimethylamine acetate is decomposed upon heating in the presence of a catalyst, viz. molybdenum oxide. Thereafter, the desired product is isolated by conventional techniques.

1 Claim, No Drawings

METHOD OF PREPARING DIMETHYLACETAMIDE IN PRESENCE OF MoO₃ CATALYST

The present invention relates to the preparation of amides and, more specifically, to a method for the preparation of dimethylacetamide.

Dimethylacetamide can find an extensive use in chemical industry, especially as a solvent.

Known in the art is a method of preparing dimethylacetamide which comprises interaction of acetic acid with dimethylamine, followed by decomposition of the resulting dimethylamine acetate at a temperature within the range of from 135 to 140° C. in the presence of an excessive amount of dimethylamine.

During the decomposition, which is performed in a rectification column still, water resulting from the reaction is distilled off.

The thus-prepared technically pure product is subjected to vacuum rectification. The desired product yield amounts to 62-65% by weight.

This prior art method has a disadvantage residing in a relatively low yield of the desired product, substantially long (up to 24-30 hours) duration of the decomposition process and, consequently, an incomplete decomposition of dimethylamine acetate (residual amount of the latter salt is up to 4% by weight). This results in contamination of the desired product with dimethylamine acetate, whereby the final product quality is impaired. However this product should satisfy rather strict requirements imposed on its quality (water content of at most 0.1% by weight, acetic acid contaminant content of at most 0.005% by weight, dimethylformamide contaminant content of at most 0.05% by weight), such as using it as a solvent in processes of polycondensation.

Rather long duration of the decomposition of dimethylamine acetate necessitating discontinuation of the process prior to completion of the reaction is the main disadvantage of the prior art method resulting in an impaired quality of the desired product and a decreased yield thereof.

It is an object of the present invention to increase the desired product yield.

It is another object of the present invention to reduce the process duration.

These and other objects of the present invention are accomplished by a method of preparing dimethylacetamide by reacting acetic acid with dimethylamine, followed by decomposition of the resulting dimethylamine acetate upon heating and isolation of the desired product, wherein, according to the present invention, said decomposition of dimethylamine acetate is carried out in the presence of a catalyst, viz. molybdenum oxide.

To perform the process continuously, it is advisable to carry out the decomposition of dimethylamine acetate at a temperature within the range of from 150 to 160° C.

The method of preparing dimethylacetamide in accordance with the present invention is effected in the following manner.

Acetic acid is preliminary saturated with dimethylamine in a separate apparatus. The resulting dimethylamine acetate is placed into a reactor communicating to a rectification column and a source of dimethylamine. Into a reactor a catalyst, viz. molybdenum oxide MoO₃ is charged in the powder-like condition in an amount of from 0.08 to 0.25% by weight and the mixture is heated while continuously passing dimethylamine therethrough. At a temperature of the order of 130 to 135° C. the reaction of decomposition of dimethylamine acetate occurs. From the column top an aqueous fraction is first collected containing dimethylamine which fraction in employed in further synthesis, then an aqueous solution of dimethylacetamide is collected.

After the starting point of collection of said aqueous dimethylacetamide solution the temperature in the reactor is elevated to 150°-160° C. and simultaneously a continuous supply of dimethylamine acetate into a reaction mass is started at the rate equal to the rate of distilling-off dimethylacetamide. Elevation of temperature above 160° C. is inadvisable due to ebullition of the mixture.

Afterwards, said aqueous solution of dimethylacetamide is subjected to rectification to give dimethylacetamide containing:

water at most 0.1% by weight;
acetic acid at most 0.005% by weight;
dimethylformamide at most 0.05% by weight.

Dimethylacetamide yield is 89-90% of the theoretical value (as calculated for the consumed acetic acid).

The use of MoO₃ as a catalyst in the decomposition of dimethylamine acetate makes it possible to accelerate, by about 10 times, the whole process.

After 500 hours of operation the catalyst activity remained practically unchanged.

For a better understanding of the present invention some specific examples illustrating the method of preparing dimethylacetamide are given hereinbelow.

EXAMPLE 1

160 ml of acetic acid are saturated with dimethylamine at the temperature of 45° C. for the period of 4 hours until the neutral reaction as determined by means of methyl red. As a result, 300 ml of dimethylamine acetate are obtained. This salt and 0.6 g of the catalyst, i.e. MoO₃ are heated in a current of dimethylamine at a temperature of 135 to 140° C. for a period of 20 hours with simultaneously distilling off water. After rectification of the decomposition product of dimethylamine acetate, 190 g of dimethylacetamide are obtained which corresponds to the yield of 85% by weight as calculated for acetic acid.

The resulting product has the following characteristics:

principal substance content 99.8% by weight;
water 0.05% by weight;
dimethylamine 0.08% by weight;
acetic acid 0.001% by weight.

EXAMPLE 2

30 ml of dimethylamine acetate prepared by a procedure similar to that described in the foregoing Example 1 and 0.6 g of the catalyst, i.e. MoO₃ are heated in a current of dimethylamine for the period of 2 hours. At the rectification column still temperature of from 130 to 135° C. an aqueous fraction is collected containing dimethylamine. Then collection of the second fraction is started, which fraction comprises an aqueous solution of dimethylacetamide, at a temperature within the range of from 150 to 160° C. After rectification of the aqueous solution of dimethylacetamide, 201.6 g of the desired product are obtained which corresponds to 90% of the theoretical yield as calculated for the weight of acetic acid.

Characteristics of the final product are similar to those of the product obtained in Example 1 hereinabove.

EXAMPLE 3

300 ml of dimethylamine acetate prepared by interaction of acetic acid and dimethylamine in a manner similar to that described in Example 1 hereinbefore and 0.6 g of $MoO_3$ are heated in a current of dimethylamine. At the temperature of the rectification column still of 130 to 135° C. an aqueous fraction is collected which contains dimethylamine, whereafter collection of the second fraction, i.e. an aqueous solution of dimethylacetamide, is started.

At this moment, into the reaction mass dimethylamine acetate is supplied at a rate equal to the rate of distilling-off said aqueous solution of dimethylacetamide. Temperature is gradually elevated to 150°–160° C. in mass and to 120°–130° C. in vaporous phase.

2,040 g of dimethylamine acetate are decomposed for a period of 48 hours of continuous operation to give 2,000 ml of an aqous solution of dimethylacetamide with a salt content of 0.6% by weight. After rectification 1,525 g of dimethylacetamide are obtained which corresponds to 90% by weight of the theoretical yield as calculated for acetic acid.

Conversion degree, with respect to acetic acid, is as high as 99–99.5%.

What is claimed is:

1. A method of preparing dimethylacetamide comprising reacting acetic acid with dimethylamine, decomposing the resulting dimethylamine acetate at a temperature ranging from 150 to 160° C., in the presence of a finely divided catalyst, molybdenum oxide, $MoO_3$, varying from about 0.08 to .25%, by weight of the reactants, to form dimethylacetamide and water, followed by isolation of the desired product.

* * * * *